(12) United States Patent
Schmitt et al.

(10) Patent No.: US 12,364,585 B2
(45) Date of Patent: Jul. 22, 2025

(54) STRAW FOR THE PRESERVATION OF A PREDETERMINED DOSE OF LIQUID-BASED SUBSTANCE

(71) Applicant: IMV TECHNOLOGIES, Saint Ouen sur Iton (FR)

(72) Inventors: Eric Schmitt, Villaines-la-Juhel (FR); Jean-Charles Gorges, Chenay (FR)

(73) Assignee: IMV TECHNOLOGIES, Saint Ouen sur Iton (FR)

( * ) Notice: Subject to any disclaimer, the term of this patent is extended or adjusted under 35 U.S.C. 154(b) by 411 days.

(21) Appl. No.: 17/014,619

(22) Filed: Sep. 8, 2020

(65) Prior Publication Data

US 2020/0397551 A1    Dec. 24, 2020

Related U.S. Application Data

(62) Division of application No. 16/052,433, filed on Aug. 1, 2018, now abandoned.

(30) Foreign Application Priority Data

Aug. 1, 2017 (FR) ........................................ 1757373

(51) Int. Cl.
*A61D 19/02* (2006.01)
*A01N 1/147* (2025.01)
(Continued)

(52) U.S. Cl.
CPC ............ *A61D 19/024* (2013.01); *A01N 1/147* (2025.01); *A61B 10/0058* (2013.01); *G01N 21/78* (2013.01)

(58) Field of Classification Search
CPC ................ A61D 19/024; A01N 1/0268; A61B 10/0058; G01N 21/78
(Continued)

(56) References Cited

U.S. PATENT DOCUMENTS 6,472,036 B2    10/2002  Saint-Ramon
7,056,727 B2     6/2006  Saint-Ramon et al.
(Continued)

FOREIGN PATENT DOCUMENTS

EP    0 873 726 A1    10/1998
FR       995878 A    12/1951
(Continued)

OTHER PUBLICATIONS

Shoucheng Dong, Zhen Li, and Jingui Qin, New Carbazole-Based Fluorophores: Synthesis, Characterization, and Aggregation-Induced Emission Enhancement, Nov. 1, 2008, Journal of Physical Chemistry, vol. 113, pp. 434-441 (Year: 2008) (Year: 2008).*

(Continued)

*Primary Examiner* — Michael L Hobbs
*Assistant Examiner* — Lenora A Abel
(74) *Attorney, Agent, or Firm* — FISHERBROYLES, LLP; Roger L. Browdy; James E. Mrose

(57) ABSTRACT

The straw comprises a tube (11) and a gas-permeable liquid-tight stopper (12), which stopper is disposed in the tube closer to one end (16) of the tube than another end (17) of the tube, which tube and which stopper are configured for the stopper to be able to slide in the tube towards the other end (17), said tube being transparent or translucent, said stopper comprising an identifier component (13) configured to emit, when it is illuminated with ultraviolet light, light of which the spectrum comprises at least one peak having a crest of predetermined wavelength in visible light, whereas when it is illuminated by visible light said identifier component does not emit said light of which the spectrum comprises said peak.

10 Claims, 1 Drawing Sheet

(51) Int. Cl.
*A61B 10/00* (2006.01)
*G01N 21/78* (2006.01)

(58) Field of Classification Search
USPC ...................................................... 435/307.1
See application file for complete search history.

(56) References Cited

U.S. PATENT DOCUMENTS

| | | | |
|---|---|---|---|
| 7,252,988 | B2 | 8/2007 | Saint-Ramon |
| 2009/0172898 | A1* | 7/2009 | Kramer .................. D06L 4/686 8/648 |
| 2016/0228101 | A1* | 8/2016 | Schmitt ................ A61D 19/024 |

FOREIGN PATENT DOCUMENTS

| | | |
|---|---|---|
| FR | 2 824 255 A1 | 11/2002 |
| FR | 2824256 A1 | 11/2002 |
| GB | 669265 | 4/1952 |
| WO | 2010/070533 A1 | 6/2010 |
| WO | 2014063052 A1 | 4/2014 |
| WO | 2014167215 A1 | 10/2014 |
| WO | WO-2015055929 A1 * | 4/2015 ........... A01N 1/0263 |

OTHER PUBLICATIONS

Dong et al., Carbazole-bases fluorophores . . . (Year: 2008).*
Shoucheng Dong, Zhen Li, and Jingui Qin, New Carbazole-Based Fluorophores: Synthesis, Characterization, and Aggregation-Induced Emission Enhancement, Nov. 1, 2008, Journal of Physical Chemistry, vol. 113, pp. 434-441 (Year: 2008).
Cryo Bio System Groupe I.M.V. Technologies, "CBS High Security Straws," www.dmdevsites.com/fertitech/wp-content/suppliers-brochures/CryoBioSystem/CryoBioSystem_High_Security_straws.pdf (Year: 2010).

* cited by examiner

STRAW FOR THE PRESERVATION OF A PREDETERMINED DOSE OF LIQUID-BASED SUBSTANCE

The invention generally relates to the preservation of a predetermined dose of liquid-based substance, in particular pure or diluted animal semen; and more particularly to the straws for performing such preservation.

It is known that such a straw comprises a tube and a stopper disposed in the tube. The stopper is usually of the three-part type originally described in French patent 995.878, corresponding to British patent 669,265, i.e. formed by two plugs made from a fibrous substance enclosing a powder which, on contact with a liquid, transforms into an impermeable paste or gel adhering to the wall of the tube so that the stopper is liquid-tight.

Similar but improved stoppers are described by the French patent applications 2 824 255 and 2 824 256.

Stoppers of another type are also known, for example a stopper made from a single-piece cylinder of hydrophobic microporous material described by European patent application 0 873 726 or a stopper made from a single-piece cylinder of sintered self-sealing microporous material as described by PCT application WO 2010/070533.

In the initial state, the stopper is disposed in the neighborhood of one of the ends of the tube and it is provided that in the filled state, the dose of liquid substance which must be preserved in the straw is disposed between the stopper and the other end of the tube (the end furthest from the stopper). The tube and the stopper are configured for the stopper to be able to slide in the tube towards the end that is initially furthest from the stopper.

To fill the straw, the end closest to the stopper is placed in communication with a vacuum source while the furthest end of the tube is placed in communication with a vessel containing the substance to be introduced into the straw.

The air initially contained between the stopper and the furthest end of the tube is sucked through the stopper while the substance moves forward into the tube until it meets the stopper.

If necessary, after filling, the straw is welded close to one or both of its ends and is stored cold.

To empty the straw, if necessary after cutting the welded end portions and thawing, there is inserted into the tube by the end closest to the stopper a rod which comes to bear against the stopper. Using this rod, the stopper is made to slide in the manner of a piston towards the end furthest from the stopper, which causes the expulsion of the dose of substance which had been introduced into the straw.

From French patent application 3 004 332 there is known such a straw which is capable of being discriminated from other straws due to the fact that the stopper comprises a magnetic component configured such that a magnet, placed next to the tube opposite the stopper, then moved over a horizontal surface, is then followed by the straw.

From French patent application 3 011 731, to which corresponds U.S. patent application 2016/0228101 there is also known such a straw capable of being discriminated from other straws due to the fact that it comprises an indicator component configured to emit, at least when the straw is in the filled state, light of which the spectrum comprises at least one peak having a crest of predetermined wavelength.

The invention also aims to provide a straw capable of being discriminated from other straws in a particularly simple, convenient and economical manner.

To that end the invention provides a straw for the preservation of a predetermined dose of liquid-based substance, comprising a tube and a gas-permeable liquid-tight stopper, which stopper is disposed in the tube in the neighborhood of one end, which tube and which stopper are configured for the stopper to be able to slide in the tube towards the other end, said tube being transparent or translucent, characterized in that said stopper comprises an identifier component configured to emit, when it is illuminated with ultraviolet light, light of which the spectrum comprises at least one peak having a crest of predetermined wavelength in visible light, whereas when it is illuminated by visible light said identifier component does not emit said light of which the spectrum comprises said peak.

Thus, in normal use, in which the illumination is in visible light not comprising ultraviolet, or in any event only a tiny fraction of ultraviolet, nothing distinguishes the straw according to the invention from a conventional straw.

It will be noted that it is simple and economical to configure the stopper of a straw in order for it to comprise the aforementioned identifier component, in particular by implementing the advantageous features disclosed below, and that a simple ultraviolet lamp suffices to recognize whether a straw that is present is an ordinary straw or a straw provided to be discriminated, a simple observer being able to see the light then emitted by the indicator component of the stopper since the tube is transparent or translucent and the wavelength of the peak is in visible light According to advantageous features:
said stopper is formed by two plugs made from a braided fibrous substance enclosing a sealing agent formed by a powder, with at least one of the two plugs forming said indicator component;
said at least one plug forming said indicator component is a braid of which the threads are coated with an optical agent emitting, when it is illuminated with ultraviolet light, said light of which the spectrum comprises said peak, whereas when said optical agent is illuminated with visible light, it does not emit said light of which the spectrum comprises said peak;
said at least one plug forming said indicator component is that which forms the end of the stopper oriented towards the end of the tube closest to the stopper;
said indicator component comprises an optical brightening agent emitting, when it is illuminated with ultraviolet light, light having a bluish hue, whereas when said optical agent is illuminated with visible light, it does not emit said light having a bluish hue; and/or
said optical brightening agent is formed by derivatives of pyrene and azole.

The disclosure of the invention will now be continued with the description of embodiments given below, for the purposes of illustration and non-limitatively, with reference to the attached drawings in which.

Figure 1:
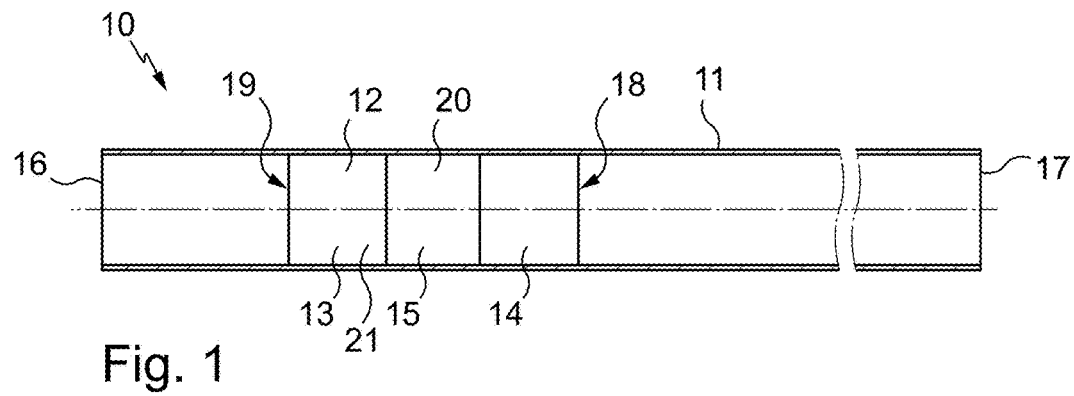
FIG. 1 is a diagrammatic view in longitudinal cross-section of a straw according to the invention, in the empty state and in visible light.

The straw 10 illustrated in FIG. 1 comprises a tube 11 and a stopper 12.

The tube 11 is conventionally made from extruded plastic material, here transparent, with an inside diameter for example of 1.6 or 2.5 mm and a length of the order of 133 mm.

The stopper 12 is of the three-part type, i.e. formed by two plugs 13 and 14 made from a fibrous substance enclosing a sealing agent 20 formed by a powder 15 which, on contact with a liquid, is capable of transforming into an impermeable paste or gel adhering to the wall of the tube 11 so that the stopper 12 is liquid-tight.

In the initial state, shown in FIG. 1, the stopper 12 is disposed in the neighborhood of the end 16 of the tube 11 and it is provided that in the filled state, the dose of liquid-based substance which must be preserved in the straw 10 is disposed between the stopper 12 and the end 17 of the tube 11 that is the furthest from the stopper 12.

In order to fill the straw 10, the end 16 is placed in communication with a vacuum source while the end 17 is placed in communication with a vessel containing the substance to be introduced into the straw.

Figure 2:
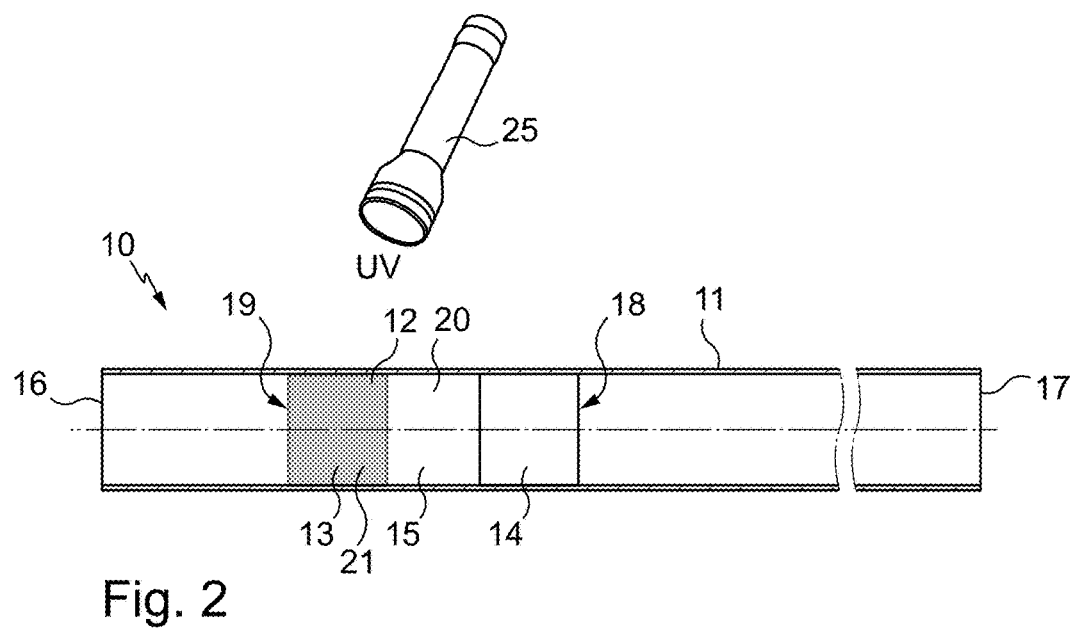
FIG. 2 is a similar view to FIG. 1, but with the zone of the straw in which the stopper is located illuminated by an ultraviolet lamp.

The air initially contained between the stopper 12 and the end 17 is sucked through the stopper 12 while the substance moves forward in the tube 11 until it encounters the stopper 12, by the end 18 thereof that faces towards the end 17 of the tube 11, that is to say the end of the stopper 12 that can be seen on the right in FIGS. 1 and 2.

The straw 10 is then in the filled state.

If necessary, after filling, the straw is welded in the neighborhood of one or both of its ends 16 and 17 and is placed in cold storage.

To empty the straw 10, if necessary after cutting the welded end portions and thawing, there is inserted into the tube 11 a rod which comes to bear on the end 19 of the stopper 12 (which end is situated on the opposite side to the end 18).

Using this rod, the stopper 12 is made to slide in the manner of a piston towards the end 17 or the end which corresponds after cutting the welded portion, which causes the expulsion of the dose of substance 21 which had been introduced into the straw.

To enable the straw 10 to be discriminated from other straws, the plug 13 comprises an optical agent 21.

It is known that an optical agent is formed by molecules that are not visible in visible light but visible when they are illuminated by ultraviolet light.

These are thus fluorescent molecules, the excitation wavelength (received light) being different from the emission wavelength (emitted light).

The optical agent 21 here is an optical brightening agent which absorbs the ultraviolet radiation of wavelength comprised between 300 and 400 nm to re-emit that energy by a visible radiation of wavelength comprised between 400 and 500 nm (bluish hue).

Here, the optical brightening agent 21 is formed by derivatives of pyrene and azole.

Here, the plug 13 is a braid of which the threads have been clad with optical brightening agent 21 by coating in an aqueous medium.

FIG. 2 shows the straw 10 in course of being illuminated with a torch 25 of which the bulb is an ultraviolet LED. For reasons of convenience, the torch 25 is represented here miniaturized relative to the straw 10 whereas in reality, the dimensions of the torch should be greater than the dimensions of the straw.

As the tube 11 is of transparent plastic material, the UV light emitted by the torch 25 illuminates the stopper 12, and thus the plug 13, such that the optical brightening agent 21 contained in the plug 13 emits light having a bluish hue.

On the contrary, when a conventional straw is illuminated by the ultraviolet light emitted by the torch 25, its stopper 12, which does not comprise any optical brightening agent, does not emit light having a blueish hue and thus maintains the same appearance or substantially the same appearance.

It is thus possible to recognize whether or not the straw 10 has been provided to be discriminated.

It will be noted that a simple ultraviolet lamp, which is a commercially-available item, suffices to recognize whether a straw that is present is an ordinary straw or a straw provided to be discriminated, a simple observer being able to see the light then emitted by the plug 13 since the tube 11 is transparent and the wavelength of the peak 22 is in visible light.

The recognition of the straw 10 may be carried out both in the initial state of the straw 10 (empty) and in the state filled with the dose of liquid substance to be kept.

Here, the plug which serves as an indicator component (plug 13) is that which forms the end 19 oriented towards the end 16 of the tube 11 which is the closest to the stopper 12 in the initial state of the straw 10, that is to say the plug the furthest from the liquid-based substance which the straw in the filled state contains.

The contacts of the substance with the plug 13 serving as indicator component are thus limited, but in any case, it has been verified by the applicant that the optical brightening agent used here (formed from derivatives of pyrene and azole) is not toxic for spermatozoa.

Figure 3:
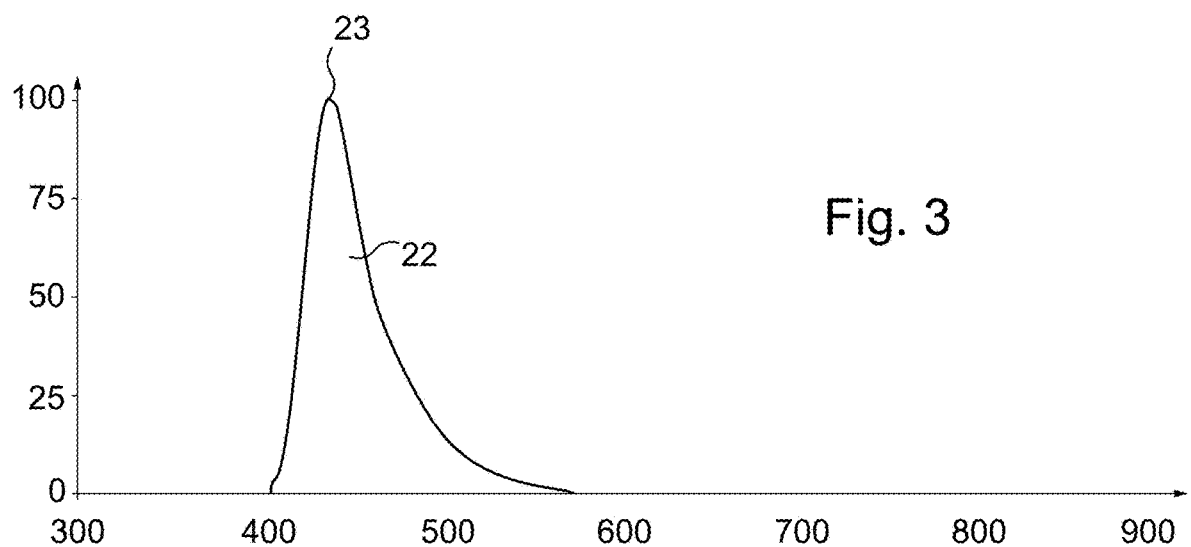
FIG. 3 is a graph illustrating the spectrum of the light emitted by an optical brightening agent comprised by the stopper of the straw when it is illuminated with ultraviolet light.

FIG. 3 is a graph illustrating the spectrum of the light emitted by an optical brightening agent contained by the plug 13 of the stopper 12, when that optical brightening agent is illuminated with ultraviolet light.

In the graph of FIG. 3, the wavelengths in nm are along the abscissa axis and the relative intensity of the emission is along the ordinate axis.

It can be seen that the optical brightener emits light of which the spectrum comprises a peak 22 here having a crest 23 the wavelength of which is of the order of 420 nm, which corresponds to the aforementioned bluish hue; and that the peak is relatively narrow, which it typical of light from fluorescence.

The light emitted by the plug 13 has a broader spectrum but also comprises the peak 22 having the crest 23.

In this spectrum, the apex of the peak 22 located in the neighborhood of the crest 23 is clearly distinguished from the rest of the spectrum and can thus be identified relatively easily by an observer and moreover by an automatic device, for example by spectrometry (FT/IR or FX) or by chromatography (HPLC) for the checking of the chemical signature of the surface of the plug 13.

Here, the ultraviolet lamp 25 is a torch of the LED bulb has a power of 1 W and emits at the wavelength of 395 nm. As a variant, another type of ultraviolet lamp is used, for example a neon ultraviolet lamp emitting at the wavelength of 365 nm.

Here the plug 13 (and also the plug 14) is white in visible light and, as indicated above, the material of the tube 11 is transparent. As a variant, the plug 13 (and moreover the plug 14) is colored in visible light and/or the tube 11 is translucent.

In variants not illustrated, the identifier component of the stopper 12 is different from the plug 13, for example the plug 14 and/or the powder 15 or even both the plug 13, the plug 14 and the powder 15. In order for the powder 15 to be able to form an identifier component, optical brightening agent powder is added to the alginate powder which conventionally forms the powder 15.

In variants not illustrated, the stopper 12 is replaced by a stopper of different type, for example a stopper made from a single piece cylinder as described in European patent application 0 873 726 or in PCT application WO 2010/070533.

As a variant, the optical agent is of a type other than the aforementioned optical brightening agent, for example distyrylbiphenyl (DSBP) or derivatives of diaminostilbene (DAS) such as Tinopal CBS (BASF)—$C_{20}H_{20}Na_2O_8S_2$.

It is to be noted that by choosing different mixtures, it is possible to have available a range of straws each having an identifier component configured to emit light of which the spectrum comprises a unique combination of peaks of light each having a predetermined location.

Numerous other variants are possible according to circumstances, and in this connection it is to be noted that the invention is not limited to the examples described and shown.

The invention claimed is:

1. A method for recognizing a straw for the preservation of a predetermined dose of liquid-based substance, comprising:
   providing the straw, the straw comprising a tube and a gas-permeable liquid-tight stopper, which stopper is disposed in the tube closer to one end of the tube than another end of the tube opposite to said one end, which tube and which stopper are configured for the stopper to be able to slide in the tube towards the other end, said tube being transparent or translucent, wherein said stopper comprises an identifier component configured to emit, when it is illuminated with ultraviolet light, light of which the spectrum comprises at least one peak having a crest of predetermined wavelength in visible light, whereas when it is illuminated by visible light said identifier component does not emit said light of which the spectrum comprises said peak;
   illuminating the straw with ultraviolet light, which passes through the transparent or translucent tube, the identifier component emitting, when it is illuminated with the ultraviolet light, the light of which the spectrum comprises at least one peak having a crest of predetermined wavelength in visible light, whereas when it is illuminated by visible light said identifier component does not emit said light of which the spectrum comprises said peak; and
   observing the light emitted by the identifier component through the transparent or translucent tube in response to the illuminating of the straw with the ultraviolet light, to thereby recognize whether the straw is an ordinary straw or a straw discriminated from ordinary straws by presence of the identifier component.

2. A method according to claim 1, wherein said stopper is formed by two plugs made from a braided fibrous substance enclosing a sealing agent formed by a powder, with at least one of the two plugs forming said indicator component.

3. A method according to claim 2, wherein said at least one plug forming said indicator component is a braid of which the threads are coated with an optical agent emitting, when it is illuminated with ultraviolet light, said light of which the spectrum comprises said peak, whereas when said optical agent is illuminated with visible light, it does not emit said light of which the spectrum comprises said peak.

4. A method according to claim 3, wherein said at least one plug forming said indicator component is that which forms an end of the stopper oriented towards the one end of the tube closest to the stopper.

5. A method according to claim 4, wherein said indicator component comprises an optical brightening agent emitting, when it is illuminated with ultraviolet light, light having a bluish hue, whereas when said optical agent is illuminated with visible light, it does not emit said light having a bluish hue.

6. A method according to claim 3, wherein said indicator component comprises an optical brightening agent emitting, when it is illuminated with ultraviolet light, light having a bluish hue, whereas when said optical agent is illuminated with visible light, it does not emit said light having a bluish hue.

7. A method according to claim 2, wherein said at least one plug forming said indicator component is that which forms an end of the stopper oriented towards the one end of the tube closest to the stopper.

8. A method according to claim 7, wherein said indicator component comprises an optical brightening agent emitting, when it is illuminated with ultraviolet light, light having a bluish hue, whereas when said optical agent is illuminated with visible light, it does not emit said light having a bluish hue.

9. A method according to claim 2, wherein said indicator component comprises an optical brightening agent emitting, when it is illuminated with ultraviolet light, light having a bluish hue, whereas when said optical agent is illuminated with visible light, it does not emit said light having a bluish hue.

10. A method according to claim 1, wherein said indicator component comprises an optical brightening agent emitting, when it is illuminated with ultraviolet light, light having a bluish hue, whereas when said optical agent is illuminated with visible light, it does not emit said light having a bluish hue.

* * * * *